(12) United States Patent
Watrin

(10) Patent No.: US 7,071,188 B2
(45) Date of Patent: Jul. 4, 2006

(54) COMPOSITION AND METHOD FOR IMPROVING PLANT GROWTH

(75) Inventor: Clifford Watrin, Wyoming, MN (US)

(73) Assignee: Syngenta Crop Protection, Inc., Greensboro, NC (US)

( * ) Notice: Subject to any disclaimer, the term of this patent is extended or adjusted under 35 U.S.C. 154(b) by 236 days.

(21) Appl. No.: 10/170,902

(22) Filed: Jun. 13, 2002

(65) Prior Publication Data

US 2003/0130119 A1    Jul. 10, 2003

Related U.S. Application Data

(60) Provisional application No. 60/298,171, filed on Jun. 14, 2001.

(51) Int. Cl.
*A61K 31/535* (2006.01)
(52) U.S. Cl. .................. 514/229.2; 514/269; 514/341; 514/342; 514/345; 514/357; 514/365; 514/407; 514/428; 514/538; 514/539
(58) Field of Classification Search ............. 514/229.2, 514/269, 341, 342, 345, 357, 365, 407, 429, 514/538, 539, 428
See application file for complete search history.

(56) References Cited

U.S. PATENT DOCUMENTS

| 5,843,982 | A | * | 12/1998 | Leadbitter ................... 514/422 |
| 6,124,356 | A | * | 9/2000 | Tseriotis et al. ............ 514/538 |
| 6,235,684 | B1 | | 5/2001 | Knauf-Beiter et al. |
| 6,559,136 | B1 | * | 5/2003 | Mauler-Machnik et al. .. 514/63 |

OTHER PUBLICATIONS

Database CROPU, Accession No. 2002-86756, (Fayetteville, Ark., USA), Rothrock, C.S. et al, Report of the Cottonseed Treatment Committee for 1999, Proc. Beltwide Cotton Conf. 2000, Wol. 1, pp. 119-123. See Abstract.

* cited by examiner

*Primary Examiner*—S. Mark Clardy
(74) *Attorney, Agent, or Firm*—Jacqueline Haley

(57) ABSTRACT

The present invention relates to plant-protecting active ingredient mixtures having synergistically enhanced action and to a method of improving the growth of plants, comprising applying to the plants or the locus thereof at least three active ingredient components together. Specifically, a mixture of fludioxonil (I), metalaxyl (II) and a strobilurin fungicide (III) achieves markedly enhanced action against plant pathogens and is suitable for improving the growth of plants when applied to plants, parts of plants, seeds, or at their locus of growth.

30 Claims, No Drawings

COMPOSITION AND METHOD FOR IMPROVING PLANT GROWTH

This application claims the benefit of Provisional Application No. 60/298,171, filed Jun. 14, 2001.

Composition and Method for Improving Plant Growth

The present invention relates to plant-protecting active ingredient mixtures having synergistically enhanced action and to a method of improving the growth of plants, comprising applying to the plants or the locus thereof at least three active ingredient components together.

It has now been found, completely surprisingly, that a mixture of fludioxonil (I), metalaxyl (II) and a strobilurin fungicide (III) achieves markedly enhanced action against plant pathogens and is suitable for improving the growth of plants when applied to plants, parts of plants, seeds, or at their locus of growth.

Active ingredient I is fludioxonil. See, for example, the Pesticide Manual, 11th Ed. (1997), The British Crop Protection Council, London, page 566.

Active ingredient II includes metalaxyl; metalaxyl consisting of more than 70% by weight of the R-enantiomer; metalaxyl consisting of more than 85% by weight of the R-enantiomer; metalaxyl consisting of more than 92% by weight of the R-enantiomer; metalaxyl consisting of more than 97% by weight of the R-enantiomer; and mefenoxam (i.e., R-metalaxyl or metalaxyl-M) wherein the metalaxyl component is pure R-metalaxyl which is substantially free of S-enantiomer. See, for example, the Pesticide Manual, 11th Ed. (1997), The British Crop Protection Council, London, page 792; and the Pesticide Manual, 11th Ed. (1997), The British Crop Protection Council, London, page 794.

Active ingredient III is a strobilurin fungicide such as azoxystrobin, picoxystrobin, kresoxim-methyl, or a compound of the formula:

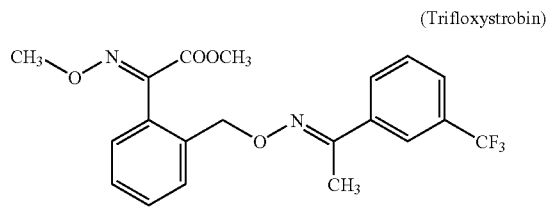

(Trifloxystrobin)

See, for example, the Pesticide Manual, 11th Ed. (1997), The British Crop Protection Council, London, pages 70 and 743.

The inventive mixture I+II+III is suitable for foliar application in living crops of plants as well as, in particular, for dressing applications on plant propagation material. The latter term embraces seeds of all kinds (fruit, tubers, grains), cuttings, cut shoots and the like. One particular field of application is the treatment of all kinds of seeds, in particular the seed treatment of maize including field corn, sweet corn and pop corn.

In addition to the three-component mixture, this invention also relates to a method of controlling fungi and improving the growth of plants, which comprises treating a site, for example a plant or a plant propagation material, that is infested or liable to be infested by fungi with a) the active ingredient I with b) the active ingredient II, and with c) the active ingredient Ill, in any desired sequence or simultaneously.

Advantageous mixing ratios by weight of the three active ingredients are I:II:III=from 10:1:1 to 1:1:10 and to 1:10:1. For example, ratios of 2.5 g: 1 g: 1 g a.i./100 kg or 2.5 g: 1 g: 2.5 g a.i./100 kg or 2.5 g:1 g:5 g a.i./100 kg or 2.5 g:1 g:10 g a.i./100 kg of seed are suitable.

The novel active ingredient mixtures I+II+III have very advantageous curative, preventive and systemic fungicidal properties for protecting cultivated plants. As has been mentioned, said active ingredient mixtures can be used to inhibit or destroy the microorganisms that occur on plants or parts of plants (fruit, blossoms, leaves, stems, tubers, roots) of different crops of useful plants, while at the same time those parts of plants which grow later are also protected from attack by such microorganisms. Active ingredient mixtures I+II+III have the special advantage of being highly active against diseases in the soil which mostly occur in the early stages of plant development. Pathogens are mainly Pythium, Tilletia, Gerlachia, Septoria, Ustilago, Fusarium, Rhizoctonia (so-called "damping off complex"). The novel mixture is also active against Oomycetes such as Phytophthora, Plasmopara, Pseudoperonospora, Bremia etc. as well as against the *Botrytis* species, *Pyrenophora, Monilinia* and further representatives of the Ascomycetes, Deuteromycetes and Basidiomycetes classes.

Suitable target crops are especially potatoes, cereals, (wheat, barley, rye, oats, rice), maize, sugar beet, cotton, millet varieties such as sorghum, sun flowers, beans, peas, oil plants such as rape, soybeans, cabbages, tomatoes, eggplants (aubergines), pepper and other vegetables and spices as well as ornamental shrubs and flowers.

The active ingredient mixtures according to the invention are especially advantageous for seed treatment of maize (field corn, sweet corn, popcorn and related crops) as well as the seed of wheat and barley.

In addition, the synergistically enhanced action of mixtures of components I, II and III manifests itself, for example, in lower rates of application, a longer duration of action and altogether higher crop yields. Such enhancements were not to be expected from the sum of the actions of the individual components.

It has now been found, that the action of the mixture of compounds of the formulae I, II and III goes far beyond their fungicidal action. It has been shown that the compounds of the formula exhibit an action termed plant growth in the frame of the instant invention. Under the term plant growth there are understood various sorts of improvements of plants which are not connected to the control of pests with the said mixture of compounds of the formulae I, II and III. For example such advantageous properties that may be mentioned are improved crop characteristics including: emergence, crop yields, protein content, more developed root system, tillering increase, increase in plant height, bigger leaf blade, less dead basal leaves, stronger tillers, greener leaf color, less fertilizers needed, less seeds needed, more productive tillers, earlier flowering, early grain maturity, less plant verse (lodging), increased shoot growth, enhanced plant vigor, increased plant stand and early germination; or any other advantages familiar to a person skilled in the art.

The active ingredient mixtures of formulae I, II and III can be used in the form of premix formulations or the active ingredients I, II and III can be applied to the area, plant or seed to be treated simultaneously or in immediate succession, if desired together with further carriers, surfactants or other application-promoting adjuvants customarily employed in formulation technology.

Suitable carriers and adjuvants can be solid or liquid and are the substances customarily employed in formulation technology, for example natural or regenerated mineral substances, solvents, dispersants, wetting agents, tackifiers, thickeners, binders or fertilizers.

The compounds of this combination are used in unmodified form or, preferably, together with the adjuvants conventionally employed in formulation technology. To this end they are conveniently formulated in known manner e.g. to emulsifiable concentrates, coatable pastes, directly sprayable or dilutable solutions, dilute emulsions, wettable powders, soluble powders, dusts, granulates, and also by encapsulation in e.g. polymer substances. As with the nature of the compositions, the methods of application, such as spraying, atomizing, dusting, scattering, coating or pouring are chosen in accordance with the intended objectives and the prevailing circumstances. Advantageous rates of application of the active ingredient mixture are normally from 0.5 g to 400 g a.i./ha, or from 1 g to 250 g a.i./ha. In the case of the treatment of seed, the rates of application are from 0.5 g to 500 g, from 1 g to 100 g, or from 5 g to 50 g a.i. per 100 kg of seed.

One method of applying a mixture of active ingredients of formulae I, II and III or an (agro)chemical composition comprising these active ingredients (with the optional addition of an insecticide such as a phenylpyrazole including fipronil or a neonicotinoid including thiamethoxam, imidacloprid, thiacloprid, clothianidin, nitenpyram or acetamiprid), is foliar application. The frequency of application and the rate of application will depend on the risk of infestation by the corresponding pathogen (fungi). However, the active ingredient mixture can also penetrate the plant through the roots via the soil (systemic action) by drenching the locus of the plant with a liquid formulation, or by applying the active ingredients in solid form to the soil, e.g. in granular form (soil application).

In a particularly suitable method, the mixture of the active ingredients of formulae I, II and III may also be applied to plant propagation material, i.e. to seeds, tubers, fruit or other plant material to be protected (e.g. bulbs) (coating) by impregnating the seeds either with a liquid formulation of the fungicides or coating them with a solid formulation (with the optional addition of an insecticide such as a phenylpyrazole including fipronil or a neonicotinoid including thiamethoxam, imidacloprid, thiacloprid, clothianidin, nitenpyram or acetamiprid). In special cases other types of application are also possible, for example the specific treatment of plant cuttings or twigs serving propagation.

The formulations are prepared in known manner, typically by intimately mixing and/or grinding the active ingredients with extenders, e.g. solvents, solid carriers and, where appropriate, surface-active compounds (surfactants).

Suitable solvents are: aromatic hydrocarbons, the fractions containing 8 to 12 carbon atoms, typically xylene mixtures or substituted naphthalenes, phthalates such as dibutyl or dioctyl phthalate, aliphatic hydrocarbons such as cyclohexane or paraffins; alcohols and glycols and their ethers and esters such as monomethyl ether, ketones such as cyclohexanone, strongly polar solvents such as N-methyl-2-pyrrolidone, dimethyl sulfoxide or dimethyl formamide, as well as vegetable oils or epoxidised vegetable oils; or water.

The solid carriers typically used for dusts and dispersible powders are calcite, talcum, kaolin, montmorillonite or attapulgite, highly dispersed silicic acid or absorbent polymers. Suitable granulated adsorptive granular carriers are pumice, broken brick, sepiolite or bentonite, and suitable non-sorptive carriers are typically calcite or dolomite.

Depending on the nature of the active ingredients to be formulated, suitable surface-active compounds are nonionic, cationic and/or anionic surfactants having good emulsifying, dispersing and wetting properties. The term "surfactants" will also be understood as comprising mixtures of surfactants.

The surfactants customarily employed in formulation technology may be found in the following literature:

"Mc Cutcheon's Detergents and Emulsifiers Annual" MC Publishing Corp., Glen Rock, N.J., 1988.

M. and J. Ash, "Encyclopedia of Surfactants", Vol. I–III, Chemical Publishing Co., New York, 1980–1981.

By way of example, application-promoting adjuvants are also natural or synthetic phospholipids of the cephalin and lecithin series, e.g. phosphatidylethanolamine, phosphatidylserine, phosphatidylglycerol and lysolecithin.

The agrochemical compositions usually comprise 0.1 to 99%, preferably 0.1 to 95%, of active ingredients of formulae I, II and III, 99.9 to 1%, preferably 99.9 to 5%, of a solid or liquid adjuvant, and 0 to 25%, preferably 0.1 to 25%, of a surfactant.

Whereas commercial products or wet or dry dressings will preferably be formulated as concentrates, the end user will normally use dilute formulations for treating plants or seeds as the case may be. However, ready to apply dilute solutions also are within the scope of the present invention.

The invention is illustrated by the following Examples wherein "active ingredient" signifies a mixture consisting of compounds I, II and III in a specific mixing ratio.

FORMULATION EXAMPLES

| Wettable powders | a) | b) | c) |
|---|---|---|---|
| Active ingredient [I:II:III = 1:6:1(a), 2:7:2(b), 3:2:3(c)] | 28% | 54% | 75% |
| Sodium lignin sulfonate | 5% | 5% | — |
| Sodium lauryl sulfate | 3% | — | 5% |
| Sodium diisobutylnaphthalene sulfonate | — | 6% | 10% |
| Octylphenol polyethylene glycol ether (7–8 mol ethylene oxide) | — | 2% | — |
| Highly dispersed silica | 5% | 10% | 10% |
| Kaolin | 59% | 23% | — |

The active ingredient is thoroughly mixed with the adjuvants and the mixture is well ground in a suitable mill to give wettable powders that can be diluted with water to suspensions of any desired concentration.

| Emulsifiable concentrate | |
|---|---|
| Active ingredient [I:II:III = 3:7:3] | 10% |
| octylphenol polyethylene glycol ether (4–5 mol ethylene oxide) | 3% |
| calcium dodecylbenzene sulfonate | 3% |
| castor oil polyglycol ether (35 mol ethylene oxide) | 4% |
| Cyclohexanone | 30% |
| Xylene mixture | 50% |

This concentrate is suitable for wet dressing plant propagation material. Emulsions of any desired concentration, which can be used for plant protection, can be prepared by diluting this concentrate with water.

| Extruder granulate | |
|---|---|
| Active ingredient [I:II:III = 1:4:2] | 15% |
| sodium lignin sulfonate | 2% |
| carboxymethyl cellulose | 1% |
| kaolin | 82% |

The active ingredient is mixed with the adjuvants; the mixture is ground and moistened with water. This mixture is extruded and then dried in a stream of air.

| Coated granulate | |
|---|---|
| Active ingredient [I:II:III = 3:5:3] | 8% |
| polyethylene glycol (MG 200) | 3% |
| kaolin | 89% |

(MG = molecular weight)

The finely ground active ingredient is applied uniformly in a mixer to the kaolin which is moistened with polyethylene glycol to give non-dusting coated granulates.

| Suspension concentrate | |
|---|---|
| Active ingredient [I:II:III = 1:6:5] | 34% |
| propylene glycol | 10% |
| nonylphenol polyethylene glycol ether (15 mol Et-oxide) | 6% |
| sodium lignin sulfonate | 10% |
| carboxymethyl cellulose | 1% |
| silicone oil (in the form of a 75% aqueous emulsion) | 1% |
| water | 38% |

The finely ground active ingredient is intimately mixed with the adjuvants to give a suspension concentrate from which suspensions of any desired concentration can be prepared by dilution with water. Such dilutions can be used to treat living plants or seeds by spraying, pouring or immersing and to protect them from infestation by fungal pests.

BIOLOGICAL EXAMPLES

The following Examples illustrate the invention in more detail. The registered trademarks and other designations denote the following products:

| | | |
|---|---|---|
| 1. Apron ® XL 3LS | (Syngenta) | Commercial seed treatment formulation of R-metalaxyl |
| 2. Maxim ® XL | (Syngenta) | Commercial seed treatment formulation of fludioxonil and R-metalaxyl (2.5:1 ratio by weight) |
| 3. CGA-301940 | | Azoxystrobin |
| 4. Captan | | N-(trichoromethylthio)cyclohex-4-ene-1,2-dicarboximide |
| 5. Allegiance-FL | | Commercial seed treatment formulation of metalaxyl. |
| 6. Maxim ® 4FS | (Syngenta) | Commercial seed treatment formulation of fludioxonil. |
| 7. Adage ® 5FS | (Syngenta) | Commercial seed treatment formulation of thiamethoxam. |
| 8. Dividend ® 3FS | (Syngenta) | Commercial seed treatment formulation of difenconazole. |

FS = flowable concentrate for seed treatment
LS = Solution for seed treatment

Example 1

Seed Treatment Test for Field Corn and Sweet Corn

Number of Reps = 4
Plot Size = 30 ft
Inoculum Rate = In-furrow, FFUSARGRAMI
Corn Variety = H-8874RR

| TRT | COMPOUND | FORM. | RATE | UNIT | 27 DAP | percent increase | 47 DAP | percent increase | 47 DAP % Vigor | percent increase |
|---|---|---|---|---|---|---|---|---|---|---|
| 1 | Check (non-inoculated) | | | | 21.3ab | 46.9 | 53.0c | 37.7 | 67.5a | −10.0 |
| 2 | Check (inoculated) | | | | 14.5b | 0.0 | 38.5d | 0.0 | 75.0a | 0.0 |
| 3 | Apron XL 3LS | 350FS | 1 | gai/100 kg | 22.8ab | 57.2 | 56.3c | 46.2 | 82.5a | 10.0 |
| 4 | Maxim XL | 324FS | 3.5 | gai/100 kg | 27.8ab | 91.7 | 67.5ab | 75.3 | 87.5a | 16.6 |
| 5 | Maxim XL | 324FS | 3.5 | gai/100 kg | 36.8a | 153.8 | 72.0ab | 87.0 | 93.8a | 25.1 |
| | CGA-301940 | 100FS | 1 | gai/100 kg | | | | | | |
| 6 | Maxim XL | 324FS | 3.5 | gai/100 kg | 34.5a | 137.9 | 76.5a | 98.7 | 83.8a | 11.7 |
| | CGA-301940 | 100FS | 2.5 | gai/100 kg | | | | | | |
| 7 | Maxim XL | 324FS | 3.5 | gai/100 kg | 34.0a | 134.5 | 69.8ab | 81.3 | 92.5a | 23.3 |
| | CGA-301940 | 100FS | 5 | gai/100 kg | | | | | | |
| 8 | Maxim XL | 324FS | 3.5 | gai/100 kg | 26.0ab | 79.3 | 72.5ab | 88.3 | 88.8a | 18.4 |
| | CGA-301940 | 100FS | 10 | gai/100 kg | | | | | | |
| 9 | CGA-301940 | 100FS | 2.5 | gai/100 kg | 13.0b | −10.3 | 42.3d | 9.8 | 80.0a | 6.6 |
| 10 | CAPTAN | 480FS | 55 | gai/100 kg | 33.0a | 127.6 | 62.0bc | 61.0 | 91.3a | 21.7 |
| | Allegiance-FL | 318FS | 2 | gai/100 kg | | | | | | |

DAP = days after planting
Comments = The tests are conducted under significant disease pressure. All seed treatment fungicide treatments are inoculated in-furrow at planting with Fusarium.
Results = Under significant disease pressure in the field, all Maxim XL and 301940 combinations provided a significant increase in stand and vigor of the plants. Combinations of Maxim XL and 301940 performed superior to Maxim XL applied alone.

Example 2

Seed Treatment Test for Field Corn and Sweet Corn

Number of Reps = 4  
Inoculum Rate = No Inoculation  
Plot Size = 30 ft  
Corn Variety = N58-D1

| TRT | COMPOUND | FORM. | RATE | UNIT | 33 DAP | percent increase | 49 DAP | percent increase |
|---|---|---|---|---|---|---|---|---|
| 1 | Check (non-inoculated) | | | | 44.5c | | 49.8c | |
| 2 | Check (inoculated) | | | | | | | |
| 3 | Apron XL 3LS | 350FS | 1 | gai/100 kg | 50.8c | 14.1 | 58.0c | 16.5 |
| 4 | Maxim XL | 324FS | 3.5 | gai/100 kg | 79.5a | 78.6 | 79.5a | 59.6 |
| 5 | Maxim XL | 324FS | 3.5 | gai/100 kg | 80.5a | 80.9 | 82.3a | 65.3 |
|   | CGA-301940 | 100FS | 1 | gai/100 kg | | | | |
| 6 | Maxim XL | 324FS | 3.5 | gai/100 kg | 80.0a | 79.8 | 81.3a | 63.3 |
|   | CGA-301940 | 100FS | 2.5 | gai/100 kg | | | | |
| 7 | Maxim XL | 324FS | 3.5 | gai/100 kg | 80.8a | 81.6 | 83.5a | 67.7 |
|   | CGA-301940 | 100FS | 5 | gai/100 kg | | | | |
| 8 | Maxim XL | 324FS | 3.5 | gai/100 kg | 64.0b | 43.8 | 67.5b | 35.5 |
|   | CGA-301940 | 100FS | 10 | gai/100 kg | | | | |
| 9 | CGA-301940 | 100FS | 2.5 | gai/100 kg | 46.5c | 4.5 | 52.8c | 6.0 |
| 10 | CAPTAN | 480FS | 55 | gai/100 kg | 47.8c | 7.4 | 54.3c | 9.0 |
|   | Allegiance-FL | 318FS | 2 | gai/100 kg | | | | |

DAP = days after planting  
Comments = The tests are conducted under significant natural disease pressure.  
Results = Under significant disease pressure in the field, all Maxim XL and 301940 combinations provide a significant increase in stand of plants. Combinations of Maxim XL and 301940 perform superior to Maxim XL applied alone.

Example 3

Evaluate The Efficacy Of Seed Treatment Products In Sweet Corn (*Pythium aphanidermatum*)

Number of Reps = 4  
Seeding Rate = 10 seeds/ft row  
Inoculation Rate = 4 gr/ft row (CUKES STRAIN)  
Plot Size = 1 row × 10 ft  
Sweet Corn variety = GSS9377

| TRT | COMPOUND | FORM. | RATE | UNIT | 6 DAP | 10 DAP | 51 DAP | percent increase |
|---|---|---|---|---|---|---|---|---|
| 1 | Check (non-inoculated) | | | | 85.00 | 85.50 | 82.3abc | 62.9 |
| 2 | Check (inoculated) | | | | 51.50 | 58.25 | 50.5d | |
| 3 | Maxim XL FS | 324FS | 3.5 | gai/100 kg | 82.50 | 84.00 | 78.5c | 55.4 |
| 4 | Apron XL 3LS | 350LS | 1 | gai/100 kg | 83.25 | 84.25 | 83.3abc | 64.9 |
|   | Maxim 4FS | 480FS | 2.5 | gai/100 kg | | | | |
|   | Adage 5FS | 600FS | 200 | gai/100 kg | | | | |
| 5 | Apron XL 3LS | 350LS | 1 | gai/100 kg | 86.25 | 87.00 | 87.8ab | 73.8 |
|   | CGA-301940 | 100FS | 5 | gai/100 kg | | | | |
| 6 | Apron XL 3LS | 350LS | 1 | gai/100 kg | 89.50 | 89.00 | 91.0a | 80.2 |
|   | CGA-301940 | 100FS | 10 | gai/100 kg | | | | |
| 7 | Apron XL 3LS | 350LS | 1 | gai/100 kg | 84.25 | 84.75 | 85.0abc | 68.3 |
|   | CGA-301940 | 100FS | 2.5 | gai/100 kg | | | | |
|   | Maxim 4FS | 480FS | 2.5 | gai/100 kg | | | | |
| 8 | Captan 4L | 480FS | 55 | gai/100 kg | 84.50 | 84.00 | 81.3bc | 60.9 |
|   | Apron XL | 350LS | 1 | gai/100 kg | | | | |
| 9 | Apron XL 3LS | 350LS | 1 | gai/100 kg | 87.75 | 83.50 | 84.8abc | 67.8 |
|   | Maxim 4FS | 480FS | 2.5 | gai/100 kg | | | | |
|   | Dividend 3FS | 360FS | 12 | gai/100 kg | | | | |

LSD (p = 0.05) = 7.8  
SD = 5.4  
CV = 6.7  
Comments = The tests are conducted under HIGH inoculum pressure. The crop is planted late in the spring season. The weather throughout the tests is warm and dry.  
Results = Under HIGH disease pressure in the field (50% reduction in stand), all Apron XL/CGA-301940 combinations provide excellent Pythium control. Similar results are obtained under low disease pressure in Example 4

Example 4

Evaluate The Efficacy Of Seed Treatment Products
In Sweet Corn (*Pythium aphanidermatum*)

| | | | | | | PERCENT VIGOR | | | Stand (Number of plants/plot) | | | |
|---|---|---|---|---|---|---|---|---|---|---|---|---|
| TRT | COMPOUND | FORM. | RATE | UNIT | 40 DAP | 55 DAP | percent increase | 8 DAP | 31 DAP | | percent increase |
| 1 | Check (non-inoculated) | | | | 72.5 | 76.3 | 11.5 | 84.75 | 78.75 | 73.75 | −2.8 |
| 2 | Check(inoculated) | | | | 70.0 | 65.0 | | 82.75 | 84.00 | 81.00 | |
| 3 | Maxim XL FS | 324FS | 3.5 | gai/100 kg | 77.5 | 82.5 | 19.2 | 87.50 | 88.25 | 85.00 | 9.0 |
| 4 | Apron XL 3LS | 350LS | 1 | gai/100 kg | 83.8 | 85.8 | 28.8 | 84.50 | 89.50 | 86.50 | 10.5 |
| | Maxim 4FS | 480FS | 2.5 | gai/100 kg | | | | | | | |
| | Adage 5FS | 600FS | 200 | gai/100 kg | | | | | | | |
| 5 | Apron XL 3LS | 350LS | 1 | gai/100 kg | 95.0 | 90.8 | 46.2 | 85.25 | 82.25 | 80.00 | 1.5 |
| | CGA-301940 | 100FS | 5 | gai/100 kg | | | | | | | |
| 6 | Apron XL 3LS | 350LS | 1 | gai/100 kg | 91.3 | 95.8 | 40.4 | 92.75 | 92.50 | 87.00 | 14.2 |
| | CGA-301940 | 100FS | 10 | gai/100 kg | | | | | | | |
| 7 | Apron XL 3LS | 350LS | 1 | gai/100 kg | 95.0 | 97.3 | 46.2 | 88.00 | 86.50 | 82.75 | 6.8 |
| | CGA-301940 | 100FS | 2.5 | gai/100 kg | | | | | | | |
| | Maxim 4FS | 480FS | 2.5 | gai/100 kg | | | | | | | |
| 8 | Captan 4L | 480FS | 55 | gai/100 kg | 82.5 | 77.5 | 26.9 | 86.25 | 85.25 | 81.25 | 5.2 |
| | Apron XL | 350LS | 1 | gai/100 kg | | | | | | | |
| 9 | Apron XL 3LS | 350LS | 1 | gai/100 kg | 86.3 | 86.3 | 32.7 | 87.50 | 88.25 | 86.00 | 9.0 |
| | Maxim 4FS | 480FS | 2.5 | gai/100 kg | | | | | | | |
| | Dividend 3FS | 360FS | 12 | gai/100 kg | | | | | | | |

LSD (p = 0.05)
SD
CV
Comments = The test is under low inoculum pressure. The crop is planted late in the spring season. The weather is warm and dry throughout the test.
Results = Under low disease pressure in the field, all Apron XL combinations significantly increase vigor of the plants.Similar results are obtained under high disease pressure in Example 3. In that test, all Apron XL combinations provided excellent Pythium aphanidermatum control.

Example 5

Evaluate The Efficacy Of Seed Treatment Products
In Sweet Corn (*Fusarium graminearum*)

Number of Reps = 4
Seeding Rate = 10 seeds/ft row
Inoculum Rate = 2.7 gr/ft of row
Plot Size = 1 row × 10 ft
Sweet corn Variety = GSS9377

| | | | | | PERCENT VIGOR | | | Stand (Number of plants/plot) | | | |
|---|---|---|---|---|---|---|---|---|---|---|---|
| TRT | COMPOUND | FORM. | RATE | UNIT | Apr. 18, 2000 | May. 4, 2000 | percent increase | Mar. 27, 2000 | Apr. 8, 2000 | May. 19,2000 | percent increase |
| 1 | Check (non-inoculated) | | | | 82.5a | 82.5 | 34.6 | 91.00 | 77.25 | 81.75a | 30.8 |
| 2 | Check (inoculated) | | | | 62.5b | 61.3 | | 71.75 | 67.00 | 62.5b | |
| 3 | Maxim XL FS | 324FS | 3.5 | gai/100 kg | 88.8a | 92.0 | 50.1 | 83.00 | 80.75 | 80.75a | 29.2 |
| 4 | Apron XL 3LS | 350LS | 1 | gai/100 kg | 92.5a | 92.0 | 50.1 | 81.50 | 81.75 | 83.75a | 34.0 |
| | Maxim 4FS | 480FS | 2.5 | gai/100 kg | | | | | | | |
| | Adage 5FS | 600FS | 200 | gai/100 kg | | | | | | | |
| 5 | Apron XL 3LS | 350LS | 1 | gai/100 kg | 91.3a | 87.5 | 42.7 | 83.50 | 77.25 | 81.50a | 30.4 |
| | CGA-301940 | 100FS | 5 | gai/100 kg | | | | | | | |
| 6 | Apron XL 3LS | 350LS | 1 | gai/100 kg | 86.3a | 79.5 | 29.7 | 78.75 | 78.50 | 79.75a | 27.6 |
| | CGA-301940 | 100FS | 10 | gai/100 kg | | | | | | | |
| 7 | Apron XL 3LS | 350LS | 1 | gai/100 kg | 93.8a | 93.8 | 52.9 | 84.00 | 80.25 | 85.00a | 36.0 |
| | CGA-301940 | 100FS | 2.5 | gai/100 kg | | | | | | | |
| | Maxim 4FS | 480FS | 2.5 | gai/100 kg | | | | | | | |

-continued

| | | | | | | | | | | |
|---|---|---|---|---|---|---|---|---|---|---|
| 8 | Captan 4L | 480FS | 55 | gai/100 kg | 75.0ab | 76.6 | 25.0 | 79.70 | 71.70 | 74.30ab | 18.9 |
| | Apron XL | 350LS | 1 | gai/100 kg | | | | | | | |
| 9 | Apron XL 3LS | 350LS | 1 | gai/100 kg | 85.0a | 88.3 | 44.0 | 87.25 | 82.75 | 87.00a | 39.2 |
| | Maxim 4FS | 480FS | 2.5 | gai/100 kg | | | | | | | |
| | Dividend 3FS | 360FS | 12 | gai/100 kg | | | | | | | |
| | | | | LSD (p = 0.05) = | 17.9 | | 19.75 | | | 12.0 | |
| | | | | SD = | 12.3 | | 13.5 | | | 8.2 | |
| | | | | CV = | 14.6 | | 16.1 | | | 10.3 | |

Comments = The tests are conducted under moderate inoculum pressure. The crop is planted late in the spring. The weather throughout the test is warm and dry.
Results = Under moderate disease pressure in the field (15% reduction in stand), all Maxim and CGA-301940 combinations provided a significant increase in stand and vigor of the plants. It performed similarly to CGA-301940 and superior to Captan.

What is claimed is:

1. A synergistically enhanced crop protection composition comprising fungicidally effective amounts of a mixture of metalaxyl (I), fludioxonil (II), a strobilurin fungicide (III) and an agronomically acceptable carrier.

2. The composition according to claim 1, wherein the ratio by weight of the mixture of I:II:III is from 10:1:1 to 1:1:10 to 1:10:1.

3. A composition according to claim 3, wherein the metalaxyl has an R-enantiomer content of more than 70% by weight.

4. A composition according to claim 3, wherein the metalaxyl has an R-enantiomer content of more the 85% by weight.

5. A composition according to claim 4, wherein the metalaxyl has an R-enantiomer content of more than 92% by weight.

6. A composition according to claim 5, which comprises the use of pure R-metalaxyl which is substantially free of S-enantiomer.

7. A composition according to claim 1, wherein the strobilurin fungicide is trifloxystorbin.

8. A composition according to claim 1, wherein the strobilurin fungicide is azoxystrobin.

9. A composition according to claim 1, wherein the strobilurin fungicide is kresoxim-methyl.

10. A composition according to claim 1, wherein the strobilurin fungicide is picoxystrobin.

11. A composition according to claim 1, which further comprises an insecticide selected from a phenylpyrazole and a neonicotinoid.

12. A composition according to claim 1, wherein the phenylpyrazole is fipronil and the neonicotinoid is selected from thiamethoxam, imidacloprid, thiacloprid, clothianidin, nitenpyram and acetamiprid.

13. Plant propagation material treated with the composition of claim 1.

14. The plant propagation material of claim 10, wherein seeds are the propagation material.

15. The plant propagation material of claim 11, wherein maize seeds are the propagation material.

16. A method of improving the growth of plants and controlling or preventing fungal infestation in plants, parts of plants, seeds, or at their locus of growth, which comprises applying in any desired sequence, simultaneously or in succession, synergistic fungicidally effective amounts of a mixture of metalaxyl, fludioxonil and a strobilurin fungicide.

17. A method according to claim 16, wherein the R-enantiomer content of the metalaxyl used is more then 70% by weight.

18. A method according to claim 16, wherein the R-enantiomer content of the metalaxyl used is more than 85% by weight.

19. A method according to claim 16, wherein the R-enantiomer content of the metalaxyl used is more than 92% by weight.

20. A method according to claim 16, wherein the metalaxyl component is pure R-metalaxyl which is substantially free of S-enantiomer.

21. A method according to claim 16, wherein the strobilurin fungicide is trifloxystorbin.

22. A method according to claim 16, wherein the strobilurin fungicide is azoxystrobin.

23. A method according to claim 16, wherein the strobilurin fungicide is kresoxim-methyl.

24. A method according to claim 16, wherein the strobilurin fungicide is picoxystrobin.

25. A method according to claim 16, which further comprises the application of an insecticide selected from a phenylpyrazole and a neonicotinoid.

26. A method according to claim 25, wherein the phenylpyrazole is fipronil and the neonicotinoid is selected from thiamethoxam, imidacloprid, thiacloprid, clothianidin, nitenpyram and acetamiprid.

27. A method according to claim 16, wherein the parts of plants are the propagation material.

28. A method according to claim 27, wherein the seeds are the propagation material.

29. A method according to claim 28, wherein maize seeds are the propagation material.

30. A pre-mix formulation comprising fungicidally effective amounts of a mixture of metalaxyl (I), fludioxonil (II), a strobilurin fungicide (III) and an agronomically acceptable carrier.

* * * * *